(12) United States Patent
Maillard et al.

(10) Patent No.: US 11,328,536 B2
(45) Date of Patent: May 10, 2022

(54) FINGERPRINT SENSOR WITH IMPEDANCE DETECTION

(71) Applicant: IDEMIA IDENTITY & SECURITY FRANCE, Courbevoie (FR)

(72) Inventors: Sylvain Maillard, Courbevoie (FR); Anne Chartier, Courbevoie (FR); Jean-Rémi Sandraz, Courbevoie (FR); Aurélie Moriceau, Courbevoie (FR)

(73) Assignee: IDEMIA IDENTITY & SECURITY FRANCE, Courbevoie (FR)

( * ) Notice: Subject to any disclaimer, the term of this patent is extended or adjusted under 35 U.S.C. 154(b) by 0 days.

(21) Appl. No.: 17/105,877

(22) Filed: Nov. 27, 2020

(65) Prior Publication Data

US 2021/0166046 A1 Jun. 3, 2021

(30) Foreign Application Priority Data

Nov. 29, 2019 (FR) ...................................... 1913508

(51) Int. Cl.
*G06V 40/40* (2022.01)
*G06V 40/13* (2022.01)
(Continued)

(52) U.S. Cl.
CPC .......... *G06V 40/45* (2022.01); *G06V 40/1318* (2022.01); *G06V 40/1329* (2022.01); *G01R 27/2623* (2013.01); *G06V 40/1365* (2022.01)

(58) Field of Classification Search
CPC ............. G06K 9/00906; G06K 9/0004; G06K 9/00053; G06K 9/00087; G06K 9/0002;
(Continued)

(56) References Cited

U.S. PATENT DOCUMENTS

| 6,665,428 B1* | 12/2003 | Gozzini | ............... | G06K 9/0002 |
| | | | | 382/124 |
| 2014/0145999 A1* | 5/2014 | Den Boer | ............. | G06F 3/0412 |
| | | | | 345/174 |

(Continued)

FOREIGN PATENT DOCUMENTS

| EP | 0786745 A2 | 7/1997 |
| WO | WO-97/14111 | 4/1997 |
| WO | WO-2018/155346 A1 | 8/2018 |

OTHER PUBLICATIONS

Shinamura et al., "Impedance-Sensing Circuit Techniques for Integration of a Fraud Detection Function Into a Capacitive Fingerprint Sensor," IEEE Sensors Journay, vol. 12, No. 5, May 1, 2012, pp. 1393-1401, 9 pages.

*Primary Examiner* — Edward F Urban
*Assistant Examiner* — Wassim Mahrouka
(74) *Attorney, Agent, or Firm* — Muncy, Geissler, Olds & Lowe, P.C.

(57) ABSTRACT

A fingerprint detection device comprising a support having a bearing surface, a sensor arranged to capture an image of a dermatoglyph of a user's finger placed on the bearing surface, and an impedance-measuring electronic circuit connected to electrodes extending on the bearing surface, conductive tracks extending on the bearing surface between the electrodes and the impedance-measuring electronic circuit. At least two of the electrodes are connected to the impedance-measuring electronic circuit by at least two conductive tracks.

7 Claims, 2 Drawing Sheets

(51) Int. Cl.
*G01R 27/26* (2006.01)
*G06V 40/12* (2022.01)

(58) Field of Classification Search
CPC ............ G06K 9/0012; G06K 9/00107; G01R 27/2623; A61B 5/053; A61B 5/0077; A61B 5/1172; A61B 2562/046; A61B 2562/0209; G01B 11/24
See application file for complete search history.

(56) References Cited

U.S. PATENT DOCUMENTS

| | | | |
|---|---|---|---|
| 2017/0124374 A1* | 5/2017 | Rowe | G06K 9/00087 |
| 2017/0262720 A1* | 9/2017 | Hwang | G06K 9/00906 |
| 2019/0046794 A1* | 2/2019 | Goodall | A61N 1/0456 |

* cited by examiner

FINGERPRINT SENSOR WITH IMPEDANCE DETECTION

BACKGROUND OF THE INVENTION

The present invention relates to the field of biometrics, and more particularly to the field of fingerprint sensors.

Biometric recognition systems are known that enable an individual to be identified by recognizing a dermatoglyph, and more particularly a fingerprint.

Such a system comprises a fingerprint detection device comprising a sensitive element associated with a finger support in such a manner that the sensitive element can capture an image of the dermatoglyph when a finger is applied against the support. Very often, the sensitive element is an optical sensor, however other technologies exist, such as capacitive detection, electric field detection, thermal detection . . . .

Fraudsters have attempted to fool biometric fingerprint recognition systems by using a fake finger having some other person's dermatoglyph made thereon. In general, such fake fingers are made of materials having properties that are different from human skin and body properties.

In order to unmask such fraudsters, the surface of the support that is in contact with the finger has been provided with electrodes that are connected by tracks to a circuit for detecting impedance between the electrodes: the impedance between electrodes (equal to the sum of the contact impedance between each of the electrodes and the skin of the finger plus the impedance inside the finger) is different with a fake finger and with a real finger.

In a conventional embodiment, the support is made of glass and the tracks and electrodes are formed by depositing an electrically conductive material on the surface of the glass. It is found that the tracks are fragile, and when a track is interrupted, e.g. by a scratch, that leads to a considerable increase in impedance, wrongly giving the impression of a fake finger.

The tracks are covered in an electrically insulating layer that also serves to provide the tracks with relative protection against abrasion resulting from contact with fingers.

Nevertheless, it can happen that the protective layer is spoiled, e.g. as a result of repeated rubbing during intensive use and/or during cleaning operations, which operations are performed more frequently when the detection device is being used intensively. This spoiling can also give rise to a conductive track being interrupted.

OBJECT OF THE INVENTION

A particular object of the invention is to improve the reliability of fingerprint detection devices.

SUMMARY OF THE INVENTION

To this end, according to the invention, there is provided a fingerprint detection device comprising a support, a sensor arranged to capture an image of a dermatoglyph of a user's finger placed on the support, and an impedance-measuring electronic circuit connected to electrodes extending on the support, conductive tracks extending on the support in order to connect together the electrodes and the impedance-measuring electronic circuit. At least two of the electrodes are each connected to the impedance-measuring electronic circuit by at least two conductive tracks.

Thus, even if one of the conductive tracks connecting the electrode to the impedance-measuring electronic circuit is cut, in particular due to abrasion or scratch, the electrode remains connected to the impedance-measuring electronic circuit by the other conductive track. The risk of all of the tracks connecting an electrode to the impedance-measuring circuit being cut is limited.

Other characteristics and advantages of the invention appear on reading the following description of a particular and nonlimiting embodiment of the invention.

BRIEF DESCRIPTION OF THE DRAWINGS

Reference is made to the accompanying drawings, in which.

DETAILED DESCRIPTION OF THE INVENTION

Figure 1:
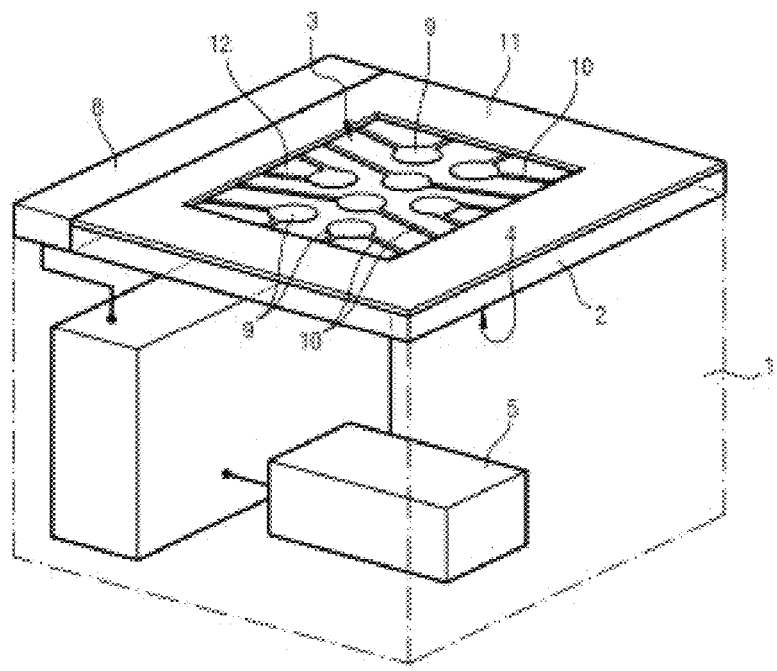
FIG. 1 is a diagrammatic view of a fingerprint detection device of the invention.
Figure 2:
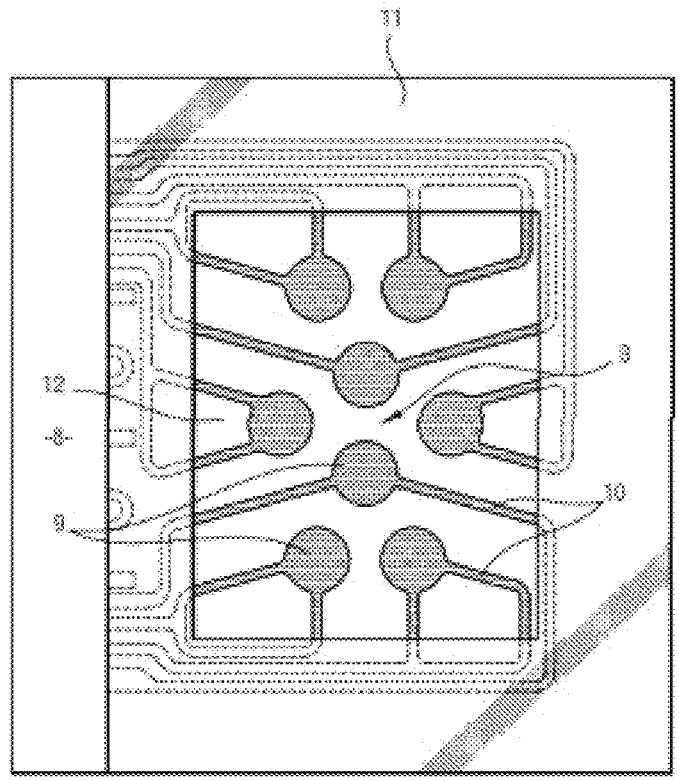
FIG. 2 is a diagrammatic view of an electrode arrangement in a first embodiment.

With reference to FIGS. 1 and 2, the fingerprint detection device of the invention comprises a housing 1 carrying a support 2, which in this example is in the form of a sheet of glass or any other transparent material. The support 2 has an outside surface 3 (facing towards the outside of the housing 1) that forms a bearing surface for a finger (the support provides a mechanical resistance preventing the finger from moving in the direction it is applied against the outside surface 3), and an inside surface 4 (facing towards the inside of the housing 1) with an optical sensor 5 mounted looking at it and connected to an electronic control unit 6 that is contained together with the optical sensor 5 in the housing 1. The optical sensor 5 is itself known, and by way of example it may be a sensor of charge coupled device (CCD) or complementary metal oxide on silicon (CMOS) type, and it is optionally arranged behind optical means comprising at least one lens. In known manner, the electronic control unit 6 comprises a processor and a memory for executing a program comprising instructions arranged in known manner for the purposes of:

- controlling the optical sensor 5 in order to acquire an image of the surface of a finger placed on the outside surface 3;
- extracting biometric characteristics from the captured image;
- comparing the extracted biometric characteristics with reference biometric characteristics and calculating a similarity score representing the result of the comparison; and
- comparing the similarity score with a threshold determined in such a manner that, when the similarity score is greater than the threshold, the probability of the extracted biometric characteristics and the reference biometric characteristics belonging to the same person is X %. This threshold is a compromise between a desired rate for false rejections (where the extracted biometric characteristics and the reference biometric characteristics are considered, wrongly, as not belonging to the same person) and a desired rate for false acceptances (where the extracted biometric characteristics and the reference biometric characteristics are considered, wrongly, as belonging to the same person).

The electronic control unit 6 is connected to an external connection connector 7 mounted on an outside surface of the housing 1. The external connection connector 7 enables the fingerprint detection device to be connected to a computer or to any other equipment capable of being supplied with the biometric data provided by the electronic control unit 6, or to a device for barring access to premises, or to any other equipment suitable for being controlled by the electronic control unit 6 as a function of the result of a biometric data comparison performed by the electronic control unit 6.

The electronic control unit 6 is connected to an impedance-measuring electronic circuit 8 (i.e. a circuit for measuring impedance), and the program of the electronic control unit 6 is arranged to compare the impedance measurements provided by the impedance-measuring electronic circuit 8 with a threshold that enables the electronic control unit 6 to distinguish between a real finger and a fake finger. The impedance-measuring electronic circuit 8 is connected to electrodes 9 via electrically conductive tracks 10. The electrodes 9 and the conductive tracks 10 are made of an electrically conductive material deposited on the outside surface 3, in this example by a vacuum deposition method (the conductive material may initially cover the entire surface and then be etched to form the electrodes, however other methods may be envisaged, e.g. such as a method of printing with an electrically conductive ink). The electrodes 9 extend in the central zone 12 of the outside surface 3. The conductive tracks 10 connecting the various electrodes 9 are spaced apart by sufficient distance to limit any risk of electrical or electromagnetic coupling between said conductive tracks 10.

The outside surface 3 is covered in an electrically insulating layer 11 (shown in FIG. 1 as being thicker than it is in reality), which layer also covers the conductive tracks 10 and presents an opening of rectangular shape leaving uncovered the central zone 12 of the outside surface 3 where the electrodes 9 are to be found. This opening defines a capture zone that lies in the field of the optical sensor 5: at least a portion of the finger must cover this zone in order to enable the optical sensor 5 to capture an image of the dermatoglyph, and the finger must be in contact with at least two electrodes in order to be able to measure impedance. In this example, the electrically insulating material constituting the electrically insulating layer 11 is silicon dioxide. In this example, the electrically insulating layer 11 has a thickness of 80 nanometers (nm).

In order to obtain a meaningful impedance measurement, the number of electrodes 9 is determined so that at least four electrodes 9 are in contact with the finger so that respective impedance measurements can be made using the electrodes 9 in six pairs. Preferably, the number of electrodes 9 is greater than four: while capturing an image of the fingerprint and given the position of the finger in the image, the electronic control unit 6 detects which electrodes 9 are in contact with the finger, and it compares a threshold with the impedances measured between said electrodes that are in contact with the finger in order to determine whether the finger is fake or real (specifically, no account must be taken of any impedance measured using an electrode that is not in contact with the finger, since any impedance measurement made with such an electrode would be very high and would wrongly be representative of a fake finger).

According to the invention, each of the electrodes 9 is connected to the impedance-measuring electronic circuit 8 via at least two conductive tracks 10.

With reference more particularly to FIG. 2, in the first embodiment of the invention, each electrode 9 is substantially circular in shape, having a diameter of about 4 millimeters (mm) in this example, and it is connected to the impedance-measuring electronic circuit 8 by two conductive tracks 10.

The electrodes 9 are distributed within the central zone 12, with electrodes 9 extending both in the vicinity of the boundaries of the central zone 12 and also in the vicinity of the middle of the central zone 12.

For each electrode 9 situated in the vicinity of one of the boundaries of the central zone 12, the conductive tracks 10 are connected to the electrode 9 on its side close to said boundary. This serves to limit the length of track left uncovered by the electrically insulating layer 11.

For each electrode 9 situated in the vicinity of the middle of the central zone 12, the conductive tracks 10 are connected to the electrode 9 at points that are diametrically opposite each other. These tracks present relative long lengths that are left uncovered by the electrically insulating layer 11: by keeping the two tracks apart from each other, any risk of a single scratch interrupting both tracks is limited.

Both conductive tracks 10 that are connected to a single electrode 9 slope relative to each other, i.e. they are not parallel to each other.

It can be understood that the risk of a conductive track being interrupted by a scratch is greater when the scratch extends in the small dimension of the conductive track, i.e. across its width. When both tracks connected to a single electrode have directions that are different, a single scratch extending in a straight line (as is most usual) cannot extend across the widths of both of the conductive tracks. Also, rubbing during cleaning operations usually takes place in a single direction, so such rubbing does not risk giving rise to scratches that extend across the widths of both of the conductive tracks connected to the same electrode.

Figure 3:
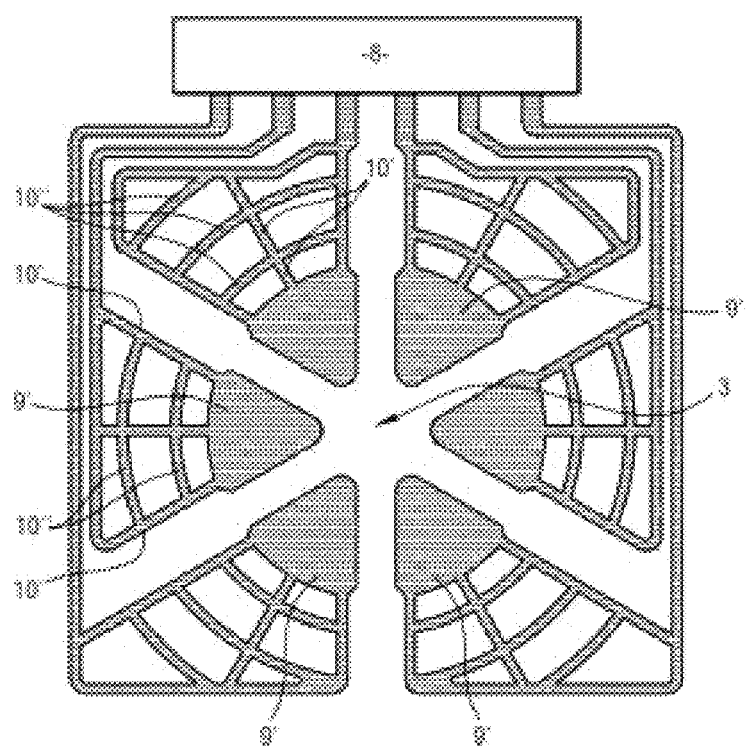
FIG. 3 is a diagrammatic view of an electrode arrangement in a second embodiment.

In the following description of the second embodiment, given with reference to FIG. 3, elements that are identical or analogous to those described above are given the same reference numerals.

The second embodiment is identical to the first embodiment, except concerning the way the electrodes and the conductive tracks are arranged.

In the second embodiment, the electrodes 9' extending in the central zone 12 of the outside surface 3 are substantially triangular in shape, each having a vertex pointing towards the middle of the central zone 12.

Each electrode 9' is connected to the impedance-measuring electronic circuit by three main conductive tracks 10' extending between said electrode 9' and the impedance-measuring electronic circuit. The conductive tracks 10' are preferably connected to one of the sides of the triangle formed by the electrode 9', this side being the side opposite from the vertex pointing towards the center of the central zone 12. The conductive tracks 10' connected to the same electrode 9' form an acute angle between one another.

Secondary conductive tracks 10" connect the main conductive tracks 10' together in pairs so as to connect each electrode 9' to the impedance-measuring electronic circuit via a network of interconnected conductive tracks 10' and 10". In this example, there are at least two secondary conductive tracks 10" for each pair of main conductive tracks 10'. It can be understood that if a main conductive track 10' has been interrupted at some point, it can nevertheless continue to convey an electric current via its non-interrupted portion to a secondary conductive track 10".

This network arrangement of conductive tracks 10' and 10" makes the connection between the electrodes 9 and the impedance-measuring electronic circuit 8 more robust against scratches.

Naturally, the invention is not limited to the embodiments described and covers any variant coming within the ambit of the invention as defined by the claims.

In particular, the detection device may be of a structure that is different from that described or shown.

The number(s), the positions, and the orientations of the main and/or secondary conductive tracks may be different from those described or shown. The conductive tracks may thus be parallel to one another.

From one electrode to another, the conductive tracks 10 may be identical in orientation or they may have different orientations. The orientation(s) of the conductive tracks may be selected as a function of an assumed or observed preferred rubbing direction: for example, if it is found that rubbing occurs mostly in the long direction of the capture zone, the conductive tracks should be oriented so that their widths extend in directions other than the preferred rubbing direction.

Concerning the number of tracks, in the event that the tracks become partially uncovered as a result of wear of the insulating layer and contact with a finger, they must not significantly influence the impedance as measured.

The number, the shapes, the areas, and the positions of the electrodes may be different from those described or shown.

It is possible to combine both of the embodiments described.

One or more of the electrodes may be connected to the impedance-measuring circuit by a single conductive track.

The shapes of the conductive tracks may be different from those shown. Advantageously, the tracks are rounded to avoid having sharp angles, in particular at the intersections between tracks (connection fillets).

The shape of the capture zone need not be rectangular, and for example it may be square, cruciform, round, or oval.

The fingerprint sensor may be optical, or it may operate using some other technology.

Preferably, the insulating layer covers the conductive tracks and a small portion of the electrodes in order to further limit any risk of the electrodes being interrupted.

The material of the insulating layer and/or its thickness may be different (its thickness may be as much as 1 micrometer (μm) or even 2 μm, for example).

Preferably, the conductive tracks and the electrodes extend directly on the outside surface 3 of the support 2 but, as a variant, the conductive tracks and/or the electrodes extend indirectly on the outside surface 3 of the support 2, i.e. they extend on one or several layers covering the outside surface 3 of the support 2. According to another example, a pattern of indium tin oxide (ITO) comprising the conductive tracks 10, and optionally the electrodes 9, extend directly on the outside surface 3, and a second pattern in metal comprising these same conductive tracks 10 and possibly these same electrodes 9, covers all or part of the pattern in indium tin oxide in order to improve electrical conduction with the finger.

The conductive tracks 10, and possibly the electrodes 9, are advantageously formed of at least one same conductive layer, i.e. in at least one same layer of conductive material.

The invention claimed is:

1. A fingerprint detection device comprising a support, a sensor arranged to capture an image of a dermatoglyph of a user's finger placed on the support, and an impedance-measuring electronic circuit connected to electrodes extending on the support, conductive tracks extending on the support in order to connect together the electrodes and the impedance-measuring electronic circuit, the fingerprint detection device being characterized in that at least two of the electrodes are each connected to the impedance-measuring electronic circuit by at least two conductive tracks, wherein the conductive tracks connected to a single electrode form between them an acute angle and at least one transverse conductive track connects together the conductive tracks connected to a single electrode.

2. A device according to claim 1, wherein the conductive tracks connected to a single electrode slope relative to each other.

3. A device according to claim 1, wherein at least one of the electrodes is substantially circular in shape.

4. A device according to claim 3, wherein the electrode of substantially circular shape has a diameter of 4 mm.

5. A device according to claim 1, wherein at least one of the electrodes is substantially triangular in shape, with a vertex pointing towards a central zone of a bearing surface of the support.

6. A device according to claim 5, wherein the conductive tracks are connected to one of the sides of the triangle formed by the electrode, this side being the side opposite from the vertex pointing towards the center of the central zone.

7. A device according to claim 1, wherein the conductive tracks are formed of at least one same conductive layer.

* * * * *